(12) United States Patent
Leach et al.

(10) Patent No.: US 8,226,907 B2
(45) Date of Patent: Jul. 24, 2012

(54) MICROFLUIDIC DEVICES AND METHODS OF MAKING THE SAME

(75) Inventors: Andrew Michael Leach, Clifton Park, NY (US); Thomas Paul Dunton, Lebanon Springs, NY (US); Christopher David Goewey, Pittsfield, MA (US); Radislav Alexandrovich Potyrailo, Niskayuna, NY (US); Caibin Xiao, Harleysville, PA (US); Prashant Vishwanath Shrikhande, Trevose, PA (US)

(73) Assignee: General Electric Company, Niskayuna, NY (US)

( * ) Notice: Subject to any disclaimer, the term of this patent is extended or adjusted under 35 U.S.C. 154(b) by 1282 days.

(21) Appl. No.: 11/440,278

(22) Filed: May 25, 2006

(65) Prior Publication Data

US 2007/0092411 A1    Apr. 26, 2007

Related U.S. Application Data

(63) Continuation-in-part of application No. 11/259,643, filed on Oct. 26, 2005, now Pat. No. 7,723,120.

(51) Int. Cl.
*B01L 3/00* (2006.01)
(52) U.S. Cl. .................................................. 422/502
(58) Field of Classification Search .................. 422/502
See application file for complete search history.

(56) References Cited

U.S. PATENT DOCUMENTS

| | | | | |
|---|---|---|---|---|
| 4,515,753 A | * | 5/1985 | Smith et al. | 422/102 |
| 5,922,615 A | * | 7/1999 | Nowakowski et al. | 436/518 |
| 6,312,901 B2 | * | 11/2001 | Virtanen | 435/6.12 |
| 7,060,227 B2 | * | 6/2006 | Staats | 422/503 |
| 2003/0005969 A1 | * | 1/2003 | Pezzuto et al. | 137/833 |
| 2005/0009101 A1 | * | 1/2005 | Blackburn | 435/7.1 |
| 2006/0001039 A1 | | 1/2006 | Zamanian | |

OTHER PUBLICATIONS

D.Jed Harrison et al., "Micromachining a Miniaturized Capillary Electrophoresis—Based Chemical Analysis System on a Chip", Science vol. 261 Aug. 13, 1993, pp. 895-897.

Stephen C. Jacobson et al., "High-speed Separations on a Microchip", Analytical Chemistry, vol. 66, No. 7, Apr. 1, 1994, pp. 1114-1118.

Larry C. Waters et al., "Microchip Device for Cell Lysis, Multiplex PCR Amplification, and Electrophoretic Sizing", Analytical Chemistry, vol. 70, No. 1, Jan. 1, 1998, pp. 158-162.

Anson Hatch et al., "Microfluidic approaches to immunoassays", SPIE vol. 3877 Sep. 1999, pp. 169-172.

E.T. Lagally et al., "Single-Molecule DNA Amplification and Analysis in an Integrated Microfluidic Device", Analytical Chemistry, vol. 73, No. 3, Feb. 1, 2001, pp. 565-570.

H. Becker and L.E. Locascio, "Polymer microfluidic devices", Elsevier Science, Talanta 56 (2002), pp. 267-287.

P.D.I. Fletcher et al., Micro reactors: principles and applications in organic synthesis, Elsevier Science, Tetrahedron 58 (2002), pp. 4735-4757.

S.A. Soper et al., "Surface modification of polymer-based microfluidic devices", Elsevier Science, Analytica Chimica Acta 470 (2002) pp. 87-99.

* cited by examiner

*Primary Examiner* — Lore Jarrett
(74) *Attorney, Agent, or Firm* — Mary Louise Stanford

(57) ABSTRACT

A microfluidic channel is provided. The microfluidic channel includes a first substrate having at least one microfluidic channel pattern. Further, the microfluidic channel includes a porous material disposed on the first substrate and occupying the at least one microfluidic channel pattern.

16 Claims, 7 Drawing Sheets

MICROFLUIDIC DEVICES AND METHODS OF MAKING THE SAME

The present patent application is a continuation-in-part application from U.S. patent application Ser. No. 11/259643, filed Oct. 26, 2005, now U.S. Pat. No. 7, 723,120, the disclosure of which is hereby incorporated by reference in its entirety.

BACKGROUND

The invention relates generally to the field of microfluidic devices. More particularly, the invention relates to materials for use in microfluidic devices and methods of making the microfluidic devices.

Microfluidic devices were first fabricated in the early 1990s in glass and silicon using traditional semiconductor processing procedures. The robustness and surface properties of these devices made them ideal for a wide range of chemical and biochemical applications including electrophoretic separations, organic synthesis, polymerase chain reaction, and immunoassays. However, high fabrication costs have driven microfluidic device fabrication to less expensive materials, such as polymers.

Typically used polymers in microfluidic devices may include polydimethylsiloxane, polycarbonate, polymethylmethacrylate, and the like. These polymer materials often have less desirable surface properties including high surface energy, poor barrier properties, and low chemical resistance. Procedures have been developed to eliminate some of these surface properties issue and to functionalize surfaces of plastic devices for the attachment of analyte molecules such as DNA, proteins, and antibodies. However, these procedures may be complex and may result in poor efficiency and poor spatial resolution of the microfluidic channels.

Typically, to get desirable surface properties the microfluidic channels are packed with one or more materials having the desirable properties. However, these packing procedures are complex, time-consuming, and often result in blocked channels.

There exists a need for a suitable material for use in microfluidic devices, which is configured to be functionalized to obtain desirable properties in the microfluidic channels. Also, there exists a need for providing a fast and efficient method of fabrication of microfluidic devices to reduce the cost of fabrication of these devices.

SUMMARY

Embodiments of the invention are directed to a microfluidic device having one or more microfluidic channels, a system employing the microfluidic device, and a method for fabricating the microfluidic device.

One exemplary embodiment of the invention is a microfluidic channel. The microfluidic channel includes a first substrate having at least one microfluidic channel pattern. Further, the microfluidic channel includes a porous material disposed on the first substrate and occupying the at least one microfluidic channel pattern.

Another exemplary embodiment of the invention is a system employing a microfluidic device. The device includes a plurality of microfluidic channels. The microfluidic channels include a porous medium disposed within a cavity that defines at least one of the plurality of microfluidic channels. The porous medium is configured to allow a flow of a sample solution there through.

Another exemplary embodiment of the invention is a method for fabricating a microfluidic device. The method includes providing a first substrate having at least one microfluidic channel pattern, and disposing a porous material in at least one of the microfluidic channel pattern. The method further includes modifying the porous material to define microfluidic channels while providing a functionalizable surface.

These and other advantages and features will be more readily understood from the following detailed description of preferred embodiments of the invention that is provided in connection with the accompanying drawings.

DETAILED DESCRIPTION OF EXEMPLARY EMBODIMENTS

A material and a method for rapid fabrication of microfluidic devices are disclosed. The microfluidic devices include one or more microfluidic channels, which are configured for applications such as chemical separations, chemical extractions (such as affinity or antibody based methods), electroosmotic pumping, and electrophoresis. The microfluidic channels may be connected to each other to form an interconnected channel network. Further, for solution-based chemistry, the channel networks may be connected to a series of reservoirs containing chemical reagents, products and/or waste to form a microfluidic device, such as a lab-on-chip. As used herein, term "lab-on-chip" refers to a device that is configured to perform a combination of analysis on a single miniaturized device for applications, such as biological, pharmaceuticals etc. In a lab-on-chip type microfluidic device, during operation the different reagents may be brought together in a specific sequence, mixed and allowed to react for a predetermined period of time in a controlled region of the channel network using processes, such as electro-kinetics or hydrodynamic pumping. For example, electro-kinetics may include electro-osmosis or electrophoresis.

Figure 1A:
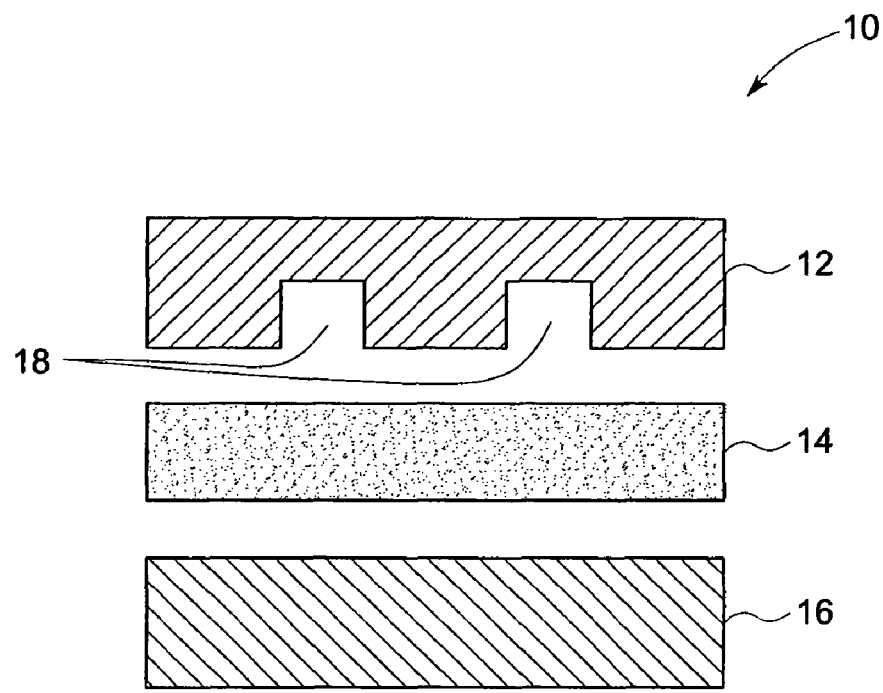
FIG. 1A is an exploded cross-sectional view of a stacking arrangement of three layers of a microfluidic device, where the stacking arrangement includes a first substrate, a porous layer, and a second substrate in accordance with exemplary embodiments of the invention.
Figure 1B:
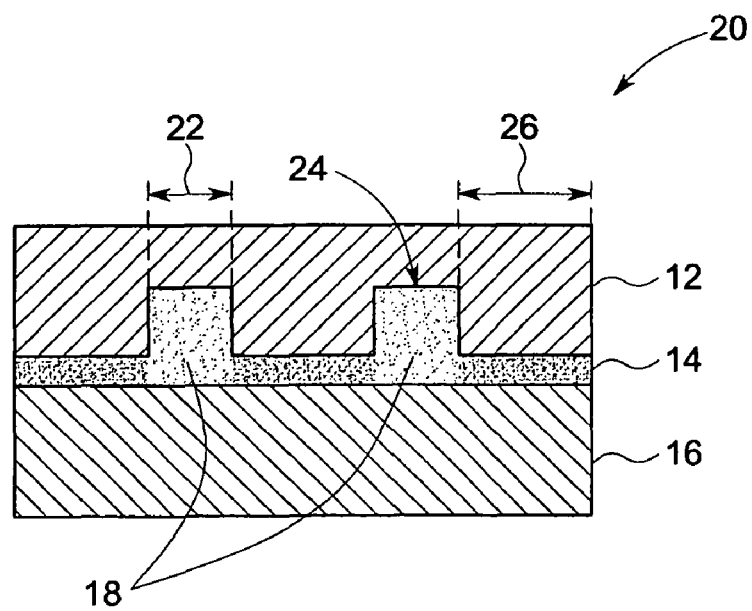
FIG. 1B is a cross-sectional view of the microfluidic device formed in accordance with the stacking arrangement of FIG. 1A.

FIG. 1A illustrates a cross-sectional view of a stacking arrangement 10 of three layers 12, 14 and 16 that form the microfluidic device 20 as illustrated in FIG. 1B. The stacking arrangement 10 includes a first substrate 12 having cavities or microfluidic channel patterns 18 defining one or more of the plurality of microfluidic channels. Depending on the material used, the microfluidic channel patterns 18 may be formed in the substrate 12 by employing patterning techniques, such as embossing, injection molding, photolithography, chemical etching, laser micro forming, or combinations thereof. In an exemplary embodiment, where the substrate 12 is made of glass, photolithography may be employed to form microfluidic channel patterns 18. Alternatively, the substrate 12 may include polymer-based material, semiconductors, ceramics, glasses, silicone, fused silica, quartz, silicon, or combinations thereof. Non-limiting examples of polymer-based materials may include SU-8, cyclic olefin copolymer (COC), poly(m-ethyl methacrylate), polystyrene, polyethylene terephthalate (PET), polycarbonate, polyvinylchloride, polydimethylsiloxane, or combinations thereof.

The stacking arrangement 10 further includes a porous material 14 and a second substrate 16. The second substrate 16 may or may not include microfluidic channel patterns depending on the desirable shape of the microfluidic channels in the device. The porous material is configured to allow a flow of a sample solution there through. In one embodiment, the porous material 14 may be produced by methods, such as, but not limited to foaming, electrospinning, self-assembly, burn-out, sol-gel, reactive gelation, reactive vapor sintering, melt down, extrusion, or combinations thereof. The porous material produced by such methods may be inorganic, organic, polymeric, hybrid, or combinations thereof. Other examples of the porous material may include porous fiberglass composite sheets, porous polymer sheets, polymeric fibers, porous membranes, silicone foam sheets, rubber foam sheets, or combinations thereof. Further, the porous material 14 may be formed from either a single layer or may include two or more layers of the porous material. In this embodiment, the two or more layers may include different porous materials.

Referring now to FIG. 2, a microfluidic device 20 is fabricated by using the stacking arrangement 10 (see FIG. 1A) having layers 12, 14 and 16. The stacked arrangement 10 is compressed by applying pressure at predetermined temperatures. The fabrication step includes compressing the stacking arrangement 10 at a temperature in a range of from about 70° C. to about 160° C., while maintaining pressures in a range of from about 50 psi to about 1000 psi. In one embodiment, the porous material 14 and one or both of the first and second substrates 12 and 16 may be permanently bonded. Upon compression, a portion of the porous material 14 disposed between the first and second substrates 12 and 16 and overlapping with the microfluidic channel pattern 18, fills the area 22 of the microfluidic channel patterns 18 to form microfluidic channels 24.

As illustrated in FIG. 1B, the porous material in the area 22 of the microfluidic channel patterns 18 experiences little or no compression force. The porous material 22 in the area 22 is configured to allow a flow of a fluid or sample solution there through. Whereas, the porous material 14 in the area 26 disposed between and in contact with the first and second substrates 12 and 16, is compressed by the applied pressure and becomes relatively denser than the porous material in the area 22. The porous material 14 in the area 26 may not allow the sample solution to flow there through, thereby defining the microfluidic channels 24 and preventing the fluids from seeping out of the microfluidic channels 24. In one embodiment, a porosity of the porous material 14 in the uncompressed regions, i.e., area 22 may be in a range of from about 30 percent to about 90 percent. However, the porosity of the porous material in the area 26 may be in a range of from about 70 percent to about 100 percent.

Further, the porous material 14 may include a non-uniform porosity. For example, the porous material 14 may include non-uniform porosity along the length of the microfluidic channel. In one embodiment, the porous material 14 may have a gradient porosity having a gradient along a direction of the liquid flow. As will be described in detail below, this non-uniform density may facilitate the function of microfluidic channels in applications, such as extraction, or separation.

In addition, one or more composite sheets may be positioned on either side of the porous material. These sheets upon compression make the surface of the porous material relatively non-porous, thereby preventing the fluids from seeping out of the microfluidic channels.

In one embodiment, the sheet of the porous material employed to fill in the microfluidic channel patterns 18 is subjected to a physical sheet-modification step. This step increases material density of one of the surfaces of the material over a predetermined thickness of the material. In another embodiment, the porous material 14 is subjected to a chemical sheet-modification step. This step modifies material chemical properties of one of the surfaces of the material over a predetermined thickness of the material. These modification steps provide modified transport properties to the species in the sample solution, which flows through the microfluidic channels 24.

In one embodiment, the porous material 14 may be functionalized to perform various applications, as will be described in detail below. In one embodiment, the porous material may be functionalized with an appropriate organic stationary phase to provide enhanced partitioning in chromatography applications. For example, in one embodiment, the porous material 14 may include glass fibers in a polymeric binder matrix. In this embodiment, the combination of glass fibers and polymeric binder provides a glass surface available inside a fluidic channel, which facilitates functionalizing the fluidic channel by means of glass surface modification methods.

Additionally, the porous material 14 may be functionalized by employing one or more of an electrolyte, an ionic solution, an antibody-based solution, a chemical reagent, a reagent emitting material, or combinations thereof. The porous material 14 may be functionalized either prior to forming the microfluidic device 20, or after forming the microfluidic device 20. For example, while employing an electrolyte, the application of a voltage across the microfluidic channels 24 may result in the formation of electro-osmotic flow of the sample fluid based on the zeta potential of the porous material, such as glass fibers. This electro-osmotic flow may be used to drive solutions through and adjacent the network of the microfluidic channels 24.

The microfluidic channels 24 may be functionalized by using chemical reagents. In one embodiment, the chemical reagents may be dispersed in the porous material before or after microfluidic device fabrication. The reagents may include one or more materials that may be desirable for a particular application. Additionally, these reagents may be positioned at selected positions in the microfluidic channels 24. For example, in a sensing application, the reagents may include chemical species positioned at a particular location of a microfluidic channel 24, where the chemical species are configured for detecting pH buffer in the microfluidic channels 24 for sensing reactions taking place downstream of the microfluidic channels 24. While the sample fluid flows through the channel, reagent immobilized in the porous material dissolves in the fluid.

In one embodiment, the porous material may be impregnated with at least one agent that is released during the operation of the microfluidic device. The release agent may have a functionality to physically, chemically or biologically modify the fluid flow passing through the microfluidic channel. For example, a chemical reagent emitting material may include a chemical reagent enclosed in an encapsulant. The chemical reagent emitting material may be configured to release the chemical reagent upon interaction with an analyte solution that is flowed in the microfluidic channel.

In applications, such as detection and sensing, the physical, chemical or biological properties of the fluids may be altered by interacting the fluid with the functionalized porous material having various reagents. Subsequently, the fluid may be identified based on the altered properties. In one embodiment, a temperature or pH of the sample fluid may be altered by a chemical reaction with a reagent incorporated into the porous material 14. In another embodiment, a biological or chemical modification of the fluid sample may be accomplished by changing the biological or chemical state of the liquid. One example of this is an unfolding or folding of a protein or nucleic acid due to a chemical reaction with a reagent incorporated into the porous material 14. For chemical modifications of the fluid in the microfluidic channel, various reagents may be employed. Non-limiting examples of reagents employed for chemical modifications of fluids may include calorimetric and fluorescent reagents. Based on the chemistry between the fluid and the reagents, these reagents may undergo a change in optical properties upon interaction with a particular fluid. The change in the optical properties may then be detected through one of the surfaces of the microfluidic channels 24.

It should be appreciated that fluids flowing in a microfluidic channel exhibit laminar flow behavior due to low Reynolds number conditions. This feature may be utilized for applications, such as particle separation and sensing. The particle separation may be based on the difference in diffusion coefficients of the particles. For example, in one embodiment, two separate fluids may be pumped through inlets at one end of the microfluidic channel, such as channels 24, these fluids may meet inside the microfluidic channels 24. Due to the laminar flow property, the two fluids may run side by side and generally may not mix except by inter-diffusion. It should be appreciated that since smaller particles diffuse faster as compared to larger particles, the smaller particles may diffuse into the parallel flow stream. Consequently, when the fluids are separated at the outlet of the microfluidic channels 24, mostly smaller particles would have diffused into the other fluid. Such a separation technique may be employed to separate blood cells from plasma. For immunoassay applications, such a technique may be used to separate large interfering molecules from samples, thereby allowing relatively more accurate analysis of analytes. Further, it is also useful to allow intermixing of fluids containing antigens with those containing large particles with immobilized antibodies, to let the immobilized antibodies react with antigens, and to later separate beads from antigens through sequential microfluidic washing or extraction steps.

In another embodiment, the microfluidic channels 24 filled with the porous material 14 may be functionalized with molecules that display an affinity (ionic, nucleic-acid or antibody-based) towards a specific target molecule. Accordingly, as a fluid having a mixture of molecules including the target molecule is passed through these channels 24, the target is selectively removed from the flow of the liquid, and concentrated on the functionalized porous material 14, such as glass fibers. Such channels may be used as a filter to remove undesired molecules or interferents. Conversely, these channels may be used as a pre-concentrator for a desirable target molecule.

In one embodiment, the porous material 14 in the microfluidic channels 24 enhances transport of the fluid from one location to another of the microfluidic device 20 by capillary action. In some embodiments, this feature may facilitate transfer of fluids between different locations in the microfluidic channels 24, where the different locations have varying dimensions and shape so as to create a difference in the capillary action between the locations. Additionally, the capillary pressure difference between these locations may be controlled by the porosity and/or hydrophilicity of the porous material. For example, the porous material may be modified to convert from a hydrophobic to ultra hydrophilic material, with water contact angle less than 10 degree, thereby changing the capillary action of the microfluidic channel.

Figure 2A:
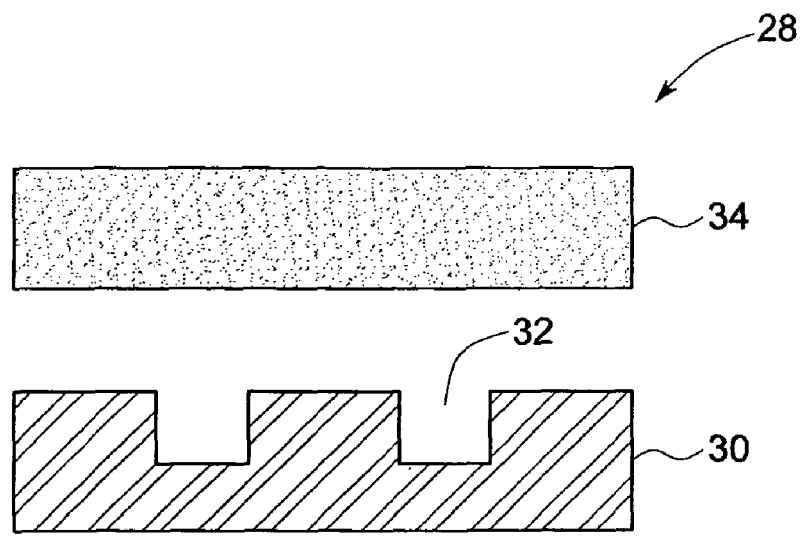
FIG. 2A is an exploded cross-sectional view of a stacking arrangement having of a microfluidic device having a functionalized porous layer, and a substrate in accordance with exemplary embodiments of the invention.
Figure 2B:
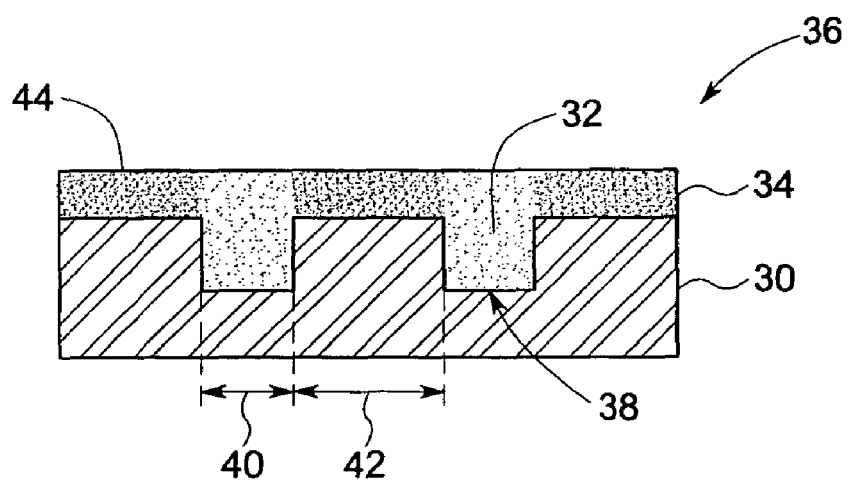
FIG. 2B is a cross-sectional view of the microfluidic device formed in accordance with the stacking arrangement of FIG. 2A.

In the illustrated embodiments of FIGS. 2A and 2B, an alternate embodiment of a microfluidic device is illustrated. The device 36 includes a substrate 30. The substrate 30 includes cavities or microfluidic channel patterns 32, which define microfluidic channels 38 in the microfluidic device 36. As illustrated in the stacking arrangement 28 of FIG. 2A, the device 36 further includes a porous material 34. The porous material 34 is positioned on the substrate 30. In one embodiment, the porous material 34 may be subjected to chemical and/or physical surface-modification step followed by fabrication of a microfluidic device.

The device 36 is formed by compressing the porous material 34 against the substrate 30. Upon compression, a portion of the porous material 34 fills the microfluidic channel patterns 32 in the areas 40 to form the microfluidic channels 38. The porous material 34 in the areas 40 may undergo little or no compression, thereby allowing passageway for the fluid flown through the microfluidic channels 38 during operation of the device 36. In areas 42, the porous material 34 is compressed to form a dense layer, effectively eliminating air from the pores in this area.

The processing fabrication step includes compressing the stacking arrangement 28 at a temperature varying in a range of from about 70° C. to about 160° C., while maintaining pressures in a range of from about 50 psi to about 1000 psi. Upon applying a processing step, the porous layer is flattened to form a layer with variable density and filling in the microfluidic channels. Due to the chemical and/or physical surface-modification steps, which make the exposed surface 44 of the porous material 34 non-porous, the microfluidic device 36 requires only two layers, the substrate 30 and the porous material 34, and does not need a second substrate, such as substrate 16 (see FIGS. 1A and 1B). Further, other modifications, such as chemical treatments, functionalizing of the porous material may also be applied to the microfluidic device 36.

Figure 3A:
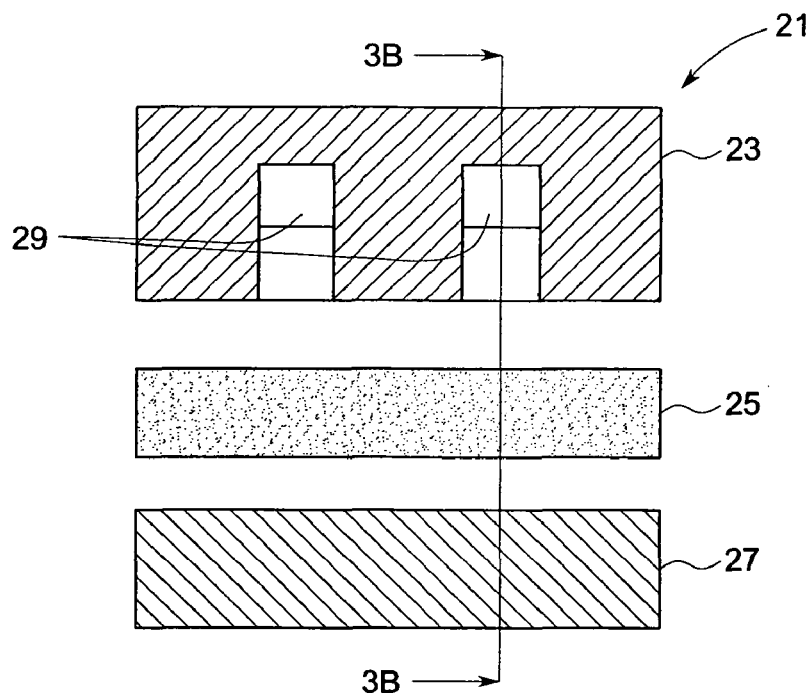
FIG. 3A is an exploded cross-sectional view of a stacking arrangement of three layers of a microfluidic device, where the stacking arrangement includes a first substrate, a porous layer, and a second substrate in accordance with exemplary embodiments of the invention.
Figure 3B:
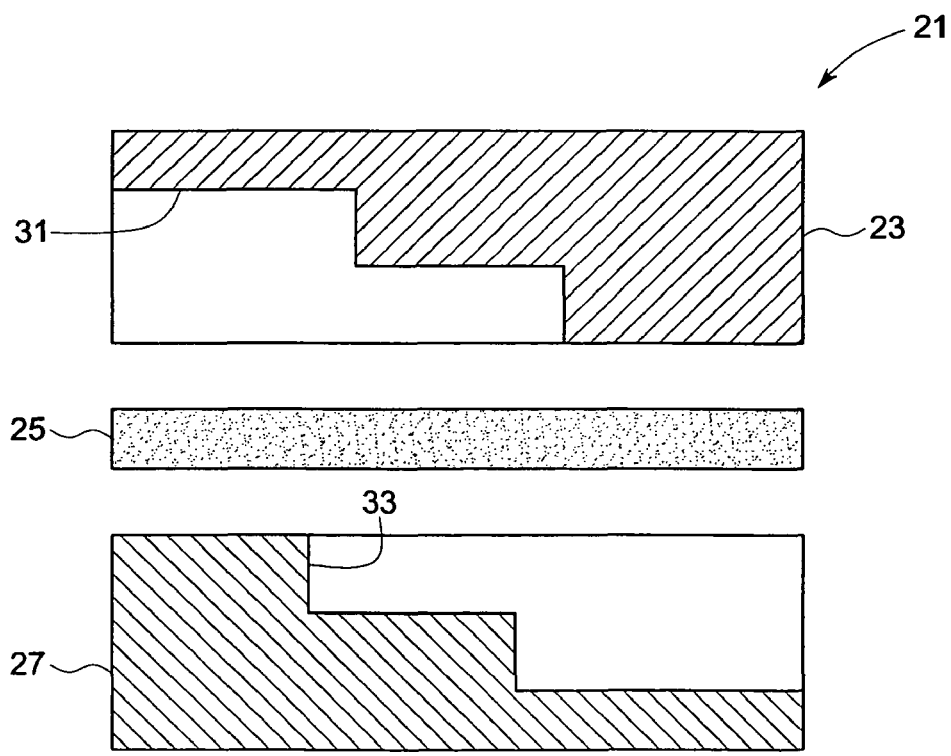
FIG. 3B is a cross-sectional view of the stacking arrangement of FIG. 3A taken along line 3B-3B.

In the illustrated embodiments of FIGS. 3A, 3B, 3C, 3D and 3E, an alternate embodiment of a microfluidic device 35 is illustrated. FIG. 3A illustrates an exploded cross-sectional view of a stacking arrangement 21 of three layers 23, 25 and 27 of the microfluidic device 35 of FIG. 3C. FIG. 3B illustrates another cross-sectional view, from a side, of the stacking arrangement 21 of FIG. 3A taken along line 3B-3B. As illustrated, the first and second substrates 23 and 27 include microfluidic channel patterns in the form of step structures 31 and 33, respectively. The two substrates 23 and 27 may have similar, complementary, or different step structures, illustrated generally as 31 and 33. Further, the stacking arrangement 21 includes a porous material 25 positioned between the substrates 23 and 27.

Figure 3C:
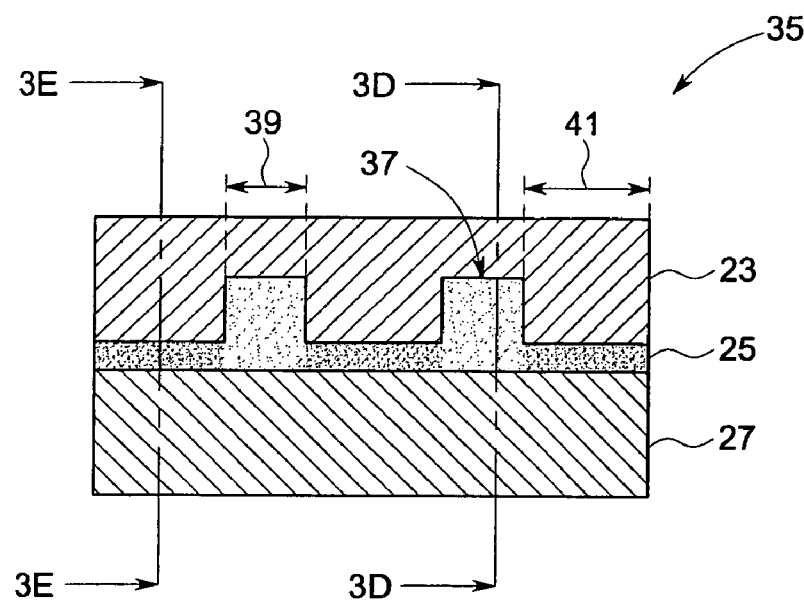
FIG. 3C is a cross-sectional view of the microfluidic device formed in accordance with the stacking arrangement of FIGS. 3A and 3B.
Figure 3D:
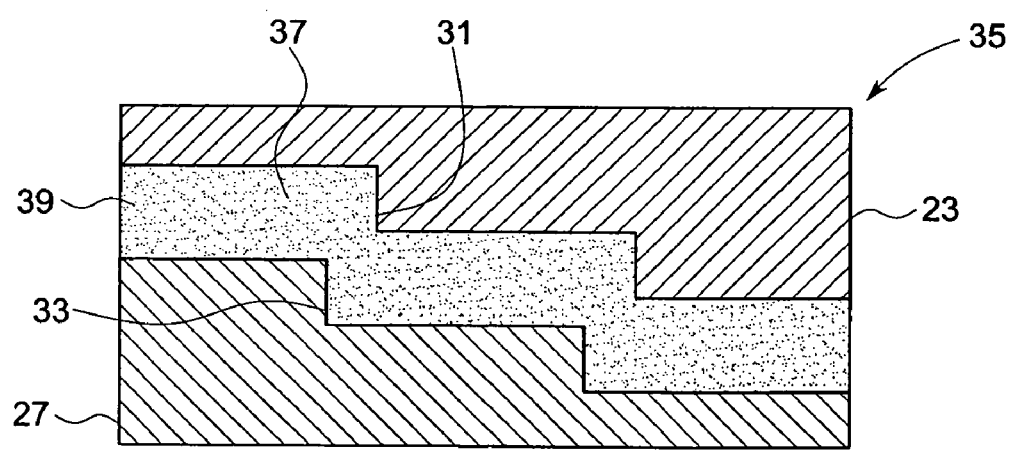
FIGS. 3D and 3E are cross-sectional views of the microfluidic device of FIG. 3C taken along lines 3D-3D and 3E-3E, respectively.
Figure 3E:
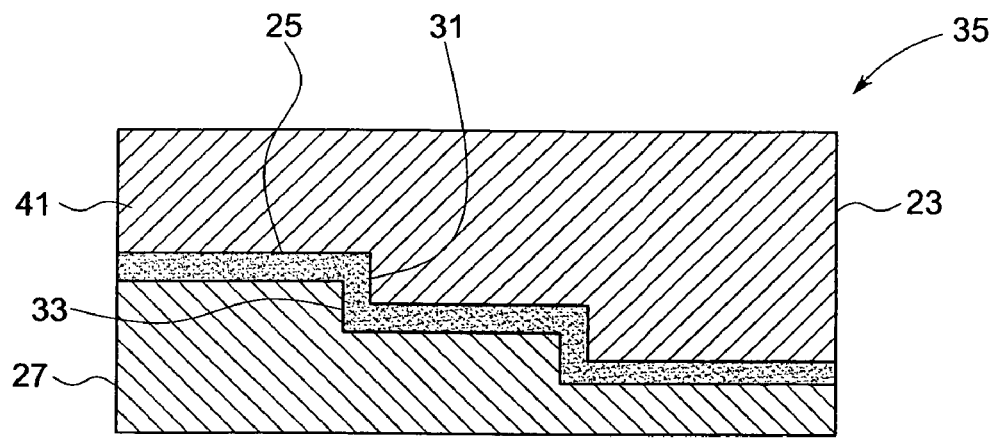

Compressing the stacking arrangement 21 forms the device 35. FIG. 3C illustrates the front view of the device 35 and FIGS. 3D and 3E illustrate the cross-sectional view of the device 35 taken along the lines 3D-3D and 3E-3E, respectively, of FIG. 3C. While forming the device 35, the substrates 23 and 27 may be positioned relative to each other such that the step structures 31 and 33 together may form microfluidic channel 37. For example, in the region 39 having the microfluidic channel 37, the step structures 31 and 33 as shown are disposed at an offset relative to each other such that the region 39 having the microfluidic channel 37 experience little or no compression and therefore has relatively less denser porous material 25 as compared to regions 41, where the porous material 25 is more dense by compression forces. The porous material 25 in these relative less dense regions 39 may undergo little or no densification. The microfluidic channel 37 formed in this embodiment may extend over different horizontal planes due to the step structures 31 and 33 of the substrates 23 and 27. In the illustrated embodiment, the microfluidic channel 37 in the region 39 may follow the steps 31 and 33 of the first and second substrates 23 and 27 to form a three-dimensional continuous microfluidic channel extending over different horizontal planes of the first and second substrates 23 and 27 along the steps 31 and 33. The porous material 25 in the region 41 may follow the step structures 31 and 33 alongside the microfluidic channel 37 to define the region of the microfluidic channel 37 and to retain the fluidic sample in the microfluidic channel 37 due to reduced porosity of the porous material 25 in the region 41. It should further be appreciated that the step structures 31 and 33 may be disposed relative to one another in a relationship that is not offset, thereby causing the regions 39 to have more dense material.

Figure 4:
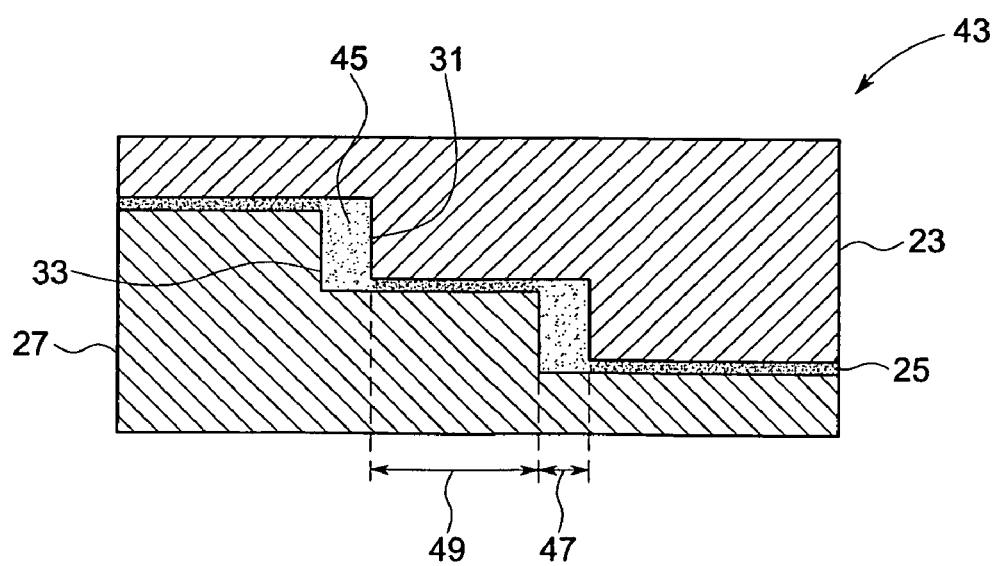
FIG. 4 is a cross-sectional view of a microfluidic device employing individual microfluidic channels at different horizontal planes of first and second substrates in accordance with exemplary embodiments of the invention.

FIG. 4 represents an alternate embodiment of the microfluidic channel 37 of FIGS. 3C and 3D. In the illustrated embodiment, the microfluidic device 43 includes individual microfluidic channels 45 that are formed on different horizontal planes defined by the steps 31 and 33 of the first and second substrates 23 and 27. The microfluidic channels 45 in the different horizontal planes may not be in communication with each other. In other words, the microfluidic channels 45 may not be continuous from one horizontal plane to another. The microfluidic channels 45 are formed by aligning the substrate 23 and 27 with respect to each other such that the porous material 25 in the regions 47 is under little or no compression force when the stacked arrangement having the substrates 23, 27 and porous material 25 is compressed to form the device 43. Accordingly, the porous material 25 in the regions 47 may not undergo densification. Whereas, the regions 49 of the porous material 25 lying outside the microfluidic channels 45 may undergo densification due to compression forces.

Figure 5:
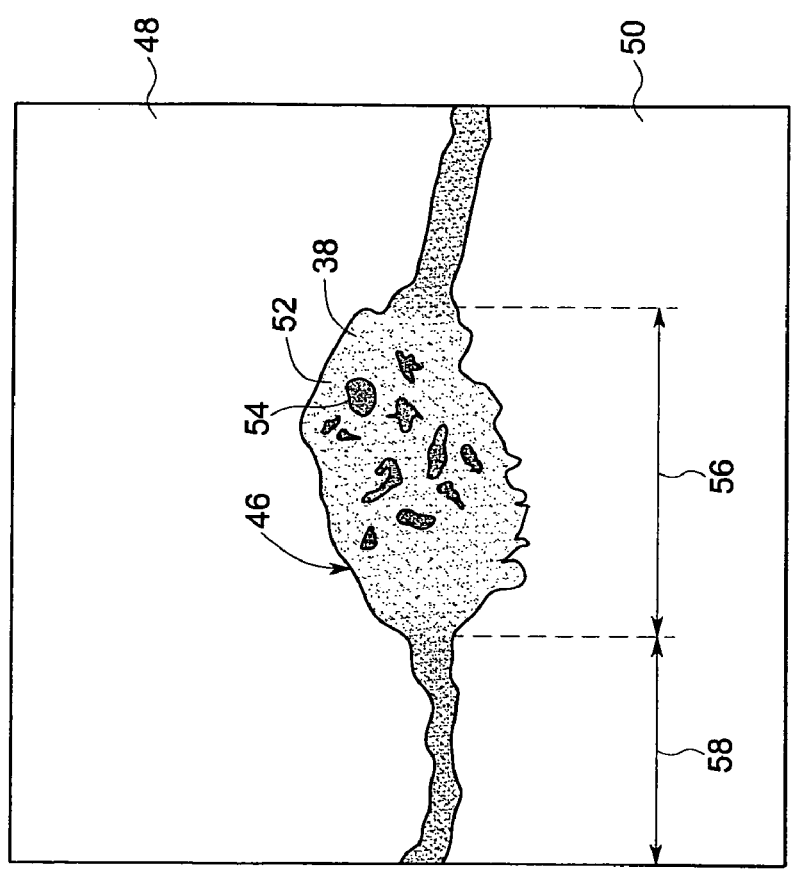
FIG. 5 is a representation of a microfluidic channel formed by compressing the porous layer in accordance with an exemplary embodiment of the invention.

FIG. 5 illustrates a microfluidic channel 46 having a porous material 52 disposed within and having pores 54. The microfluidic channel 46 is disposed between a first substrate 48 and a second substrate 50. Both the first and the second substrates 48 and 50 include microfluidic channel patterns in the region 56 to define the microfluidic channel 46. During fabrication, the portion of the porous material 52 disposed inside the area 56 experiences lesser compression forces and therefore has a higher porosity as compared to the portion of the porous material in the area 58. Accordingly, the pores 54 in the portion of the porous material 52 disposed in the area 56 are larger than the pores in other areas, such as 58, thereby allowing the flow of liquid through the microfluidic channel 46.

Figure 6:
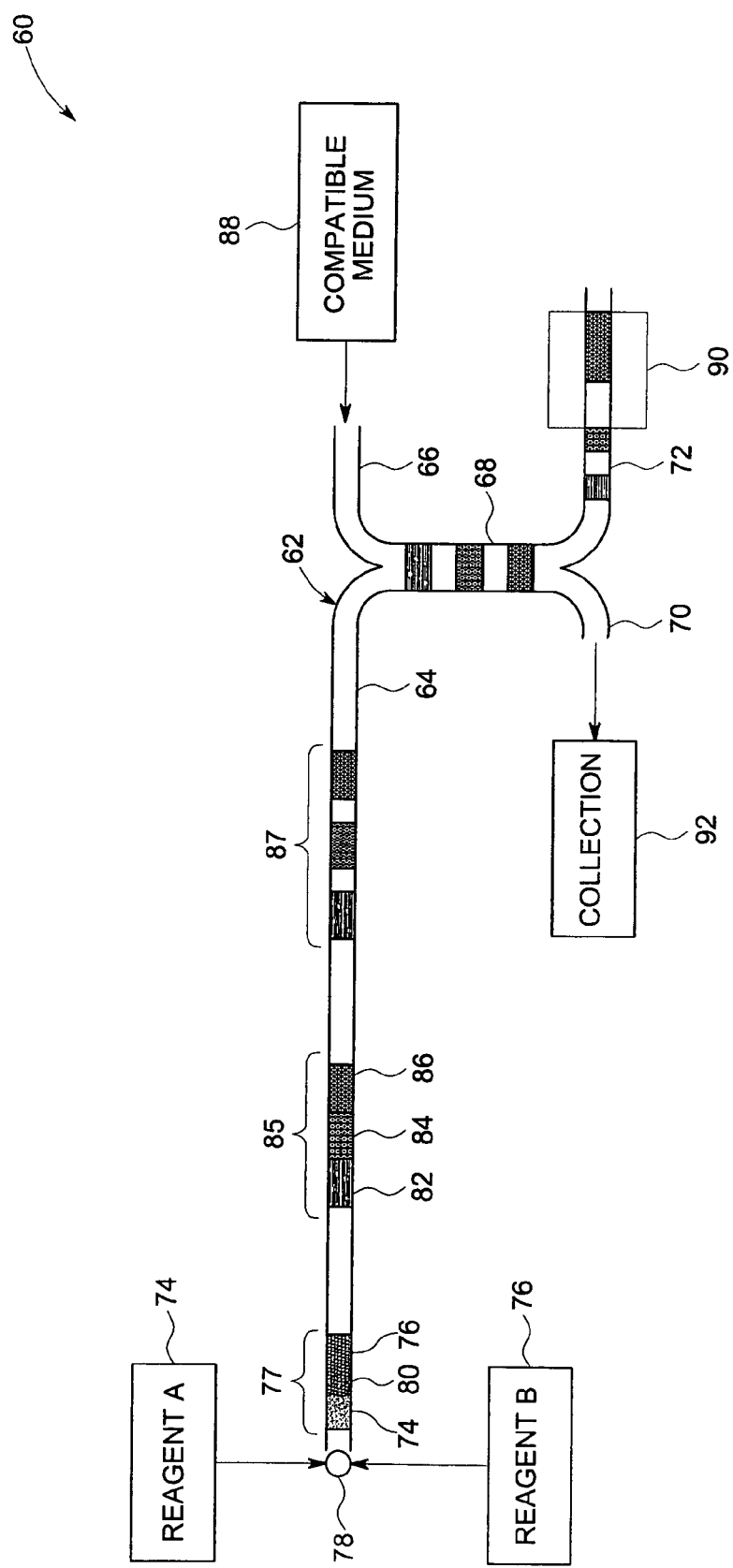
FIG. 6 is a diagrammatical illustration of a biological assay system employing a microfluidic device in accordance with an exemplary embodiment of the invention.

FIG. 6 illustrates a system 60 employing a microfluidic device 62. In an exemplary embodiment, the system 60 may be used in the pharmaceutical industry, which rely on synthesis and screening of chemical entities. The system 60 provides shortened optimization cycle times, and is cost effective due to the much lower amount of reagents required. Further, the system 60 provides the ability for a range of controls over the chemistry, environment, directly through device resident actuators.

Usually in conventional batch technology, validation and optimization of reactions tend to be the rate-limiting step. However, in system 60 auto-optimization may be carried out for biological assay or chemical assays. Additionally, the amounts of material generated by the system 60 may be increased by providing a parallel set of the microfluidic channels.

The microfluidic device 62 includes microfluidic channels 64, 66, 68, 70 and 72. The microfluidic channels 64, 66, 68, 70 and 72 may include same or different porous material (not illustrated). The reagents, namely reagent A represented by block 74 and reagent B represented by block 76, are fed in the microfluidic channel 64 of the microfluidic device 62 through the inlet 78. Once in the microfluidic channel 64, the reagents A and B 74 and 76 are allowed to react as indicated by the reference numeral 80 during the reaction stage 77 to form products 82, 84 and 86 at a product formation stage 85. Additionally, although not illustrated by-products may also be formed during the product formation stage 85. Subsequently, the products 82, 84 and 86 may be separated at the product separation stage 87 by using separation techniques, such as chromatography or electrophoresis. In one example, liquid chromatography, size exclusion chromatography or ion chromatography may be employed to separate the products 82, 84 and 86. In another example, capillary electrophoresis, or gel electrophoresis may be employed to separate the products 82, 84 and 86.

Subsequently, the separated products 82, 84 and 86 may be suspended in a compatible medium 88 introduced in the device 62 via the microfluidic channel 66. The compatible medium 88 facilitates the segregation and distribution of the three products in predetermined positions. For example, the compatible medium 88 facilitates the products 82, 84 and 86 to enter the microfluidic channel 72 to be collected as an assay at a block depicted by reference numeral 90, and the rest of the undesired by-products gets collected outside the microfluidic device 62 through the microfluidic channel 70 as depicted by the block 92. Although, not illustrated, the system 60 may further include a detector, a feedback circuitry, or both. The detector or the feedback circuitry may be in operative association with the microfluidic device 62. In one embodiment, the feedback circuitry may be configured to adjust the amount of reagents entering the microfluidic device 62.

Other applications of microfluidic devices of the invention may include conducting bio-analytical assays, such as polymerase chain reaction (PCR) at very small volumes to increase the speed of these assays and to reduce the amount of material and reagents needed. For example, the microfluidic devices may be employed for DNA sizing, RNA sizing, separation of toxins, separation of biological cells, such as viruses or bacteria, separation of molecules of inorganic ions, pharmaceuticals, narcotics, or pesticides, or separation of synthetic polymers, or separation of chemical warfare agents and hydrolysis products of chemical warfare agents. In one embodiment, DNA fragment sizing and sequencing on capillary and capillary array electrophoresis microdevices integrated electrochemical detection, and amino acid chirality analysis.

Alternatively, embodiments of the microfluidic devices of the invention may be employed for synthesis. For example, the microfluidic devices may be employed for carrying out various synthetic methods, such as flow injection analysis, continuous flow reactions, pulsed flow reactions, or segmented flow reactions. Further, the microfluidic devices may be employed for conducting reactions between synthetic analytes, such as small molecules or inorganic ions, pharmaceuticals, narcotics, pesticides, synthetic polymers, biological polymers, such as DNA or RNA, semiconductor nanoparticles, noble metals nanoparticles, or quantum dots.

Additionally, the microfluidic devices may also be employed for pre-concentration or extraction of analytes in a given fluidic sample. For example, the proteins, peptides, nucleic acids, such as DNA or RNA, toxins, biological cells, inorganic ions, pharmaceutical molecules, narcotics molecules, or pesticides molecules may be extracted from a solution by employing the microfluidic devices described above. Further, the analysis done by the microfluidic devices may be either time resolved or time based, or may be steady state.

Further, the microfluidic devices of the embodiments discussed above may be employed for detection applications. In these applications, the microfluidic devices may be employed in electronic spectroscopy, vibrational spectroscopy, microwave spectroscopy; ultraviolet-visible spectroscopy, fluorescence spectroscopy, Raman spectroscopy, surface enhanced Raman spectroscopy, metal enhanced fluorescence spectroscopy, near-infrared spectroscopy, infrared spectroscopy, or combinations thereof. In these applications, the microfluidic devices may be coupled to one or more of these spectrometers.

EXAMPLE

A glass fiber composite, AZDEL Superlite, obtained from GE Plastics, (Mount Vernon, Ind. 47620-9364) was sandwiched between four glass microscope slides (Corning Glass Works, Model 2947) such that two slides were positioned on each side of the AZDEL composite. On each side of the AZDEL the glass slides were positioned such that a 1.5 mm gap was created to form a fluidic channel. The AZDEL Superlite composite sheet and the glass slides were 1 mm thick. The sandwich structure was then compressed with moderate pressures of about 200 psi and elevated temperatures of 120° C. between two metal plates Regions where pressure was applied underwent reduction in thickness. Additionally, the compressed region bonded the glass slide AZDEL sandwich into one unit. Regions where pressure was not applied (the regions located below the gap in the glass slides) were not compress and thus formed a microfluidic channel as illustrated in FIG. 5. The dimensions of the microfluidic channel so formed were 1.0 mm ×1.5 mm channel. In this channel the composite material having the glass fiber and the polymer binder retains its bulk to allow the transport of fluids through the microfluidic channel. However, in compressed regions the AZDEL Superlite composite was compressed to a thickness of 0.150 mm each, thereby effectively sealing the microfluidic channel to prevent any fluid transport outside the channel. Similar results have been achieved by the compression of AZDEL composite between polycarbonate sheets containing micromachined channels.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while the microfluidic device is described in conjunction with separation, detection, pharmaceutical applications, it should be appreciated that the microfluidic device may find utility for any application where a microfluidic channel is employed. Additionally, while various embodiments of the invention have been described, it is to be understood that aspects of the invention may include some of the described embodiments. Accordingly, the invention is not to be seen as limited by the foregoing description, but is only limited by the scope of the appended claims.

What is claimed as new and desired to be protected by Letters Patent of the United States is:

1. A microfluidic channel, comprising:
   a first substrate comprising at least one microfluidic channel pattern;
   a porous material disposed on said first substrate and having a first porosity and a second porosity, wherein the porous material having the first porosity occupies said at least one microfluidic channel pattern, wherein the porous material having the second porosity is disposed adjacent said microfluidic channel pattern, and wherein the second porosity is less than the first porosity.

2. The microfluidic channel of claim 1, wherein said first substrate and said porous material are permanently bonded together.

3. The microfluidic channel of claim 1, further comprising a second substrate positioned such that said porous material comprising the second porosity is disposed between said first and second substrates.

4. The microfluidic channel of claim 1, wherein a surface of said porous material is modified to reduce a porosity of said surface.

5. The microfluidic channel of claim 1, wherein said porous material is functionalized.

6. The microfluidic channel of claim 1, wherein said porous material comprises one of an electrolyte, an ionic solution, an antibody-based solution, a chemical reagent, a reagent emitting material, or combinations thereof disposed in pores.

7. The microfluidic channel of claim 6, wherein said reagent emitting material comprises a chemical reagent enclosed in an encapsulant, and wherein said reagent emitting material is configured to release said chemical reagent upon interaction with an analyte solution.

8. The microfluidic channel of claim 1, wherein said porous material comprising the first porosity comprises a non-uniform porosity.

9. The microfluidic channel of claim 1, wherein said porous material comprising the first porosity comprises a gradient porosity having a gradient along a direction of the liquid flow.

10. The microfluidic channel of claim 1, wherein the first porosity is in a range from about 30 percent to about 90 percent.

11. The microfluidic channel of claim 1, wherein said first substrate comprises metals, ceramics, glasses, silicone, fused silica, quartz, silicon, polymers, or combinations thereof.

12. The microfluidic channel of claim 11, wherein said polymers comprise SU-8, cyclic olefin copolymer, poly(methyl methacrylate), polystyrene, polyethylene terephthalate, polycarbonate, or combinations thereof.

13. The microfluidic channel of claim 1, wherein said porous material comprises porous fiberglass composite sheets, porous polymer sheets, porous membranes, silicone foam sheets, rubber foam sheets, or combinations thereof.

14. The microfluidic channel of claim 1, further comprising a composite material disposed on a surface of said porous material comprising the first porosity.

15. The microfluidic channel of claim 1, wherein said microfluidic channel comprises a three dimensional continuous structure extending over two or more horizontal planes.

16. The microfluidic channel of claim 1, wherein the second porosity is formed through compression between said first and second substrates.

* * * * *